United States Patent
Dakin et al.

(10) Patent No.: US 6,409,691 B1
(45) Date of Patent: Jun. 25, 2002

(54) LIQUID BRACE

(75) Inventors: Edward B. Dakin, Lindsay; S. Adam Hacking, Montreal, both of (CA)

(73) Assignee: Daos Limited (CA)

( * ) Notice: Subject to any disclaimer, the term of this patent is extended or adjusted under 35 U.S.C. 154(b) by 0 days.

(21) Appl. No.: 09/366,344

(22) Filed: Aug. 2, 1999

(51) Int. Cl.[7] ............................................. A61F 5/00
(52) U.S. Cl. ...................... 602/5; 602/13; 128/DIG. 20
(58) Field of Search ............... 602/5, 13; 128/DIG. 20; 601/15, 152

(56) References Cited

U.S. PATENT DOCUMENTS

| | | | |
|---|---|---|---|
| 3,238,936 A | 3/1966 | Siedentop | |
| 3,671,980 A | 6/1972 | Baird | 3/20 |
| 3,889,301 A | 6/1975 | Bonner | 3/20 |
| 3,955,565 A | 5/1976 | Johnson | 128/89 |
| 4,280,489 A | 7/1981 | Johnson | 128/80 |
| 4,287,920 A | 9/1981 | Johnson | 141/85 |
| 4,331,133 A * | 5/1982 | Arkans | 602/13 |
| 4,378,009 A | 3/1983 | Rowley et al. | 128/83 |
| 4,628,918 A | 12/1986 | Johnson | 128/90 |
| 4,628,945 A | 12/1986 | Johnson | 128/80 |
| 4,655,779 A | 4/1987 | Janowiak | 623/37 |
| 4,842,608 A | 6/1989 | Marx et al. | 623/33 |
| 4,938,207 A | 7/1990 | Vargo | 128/80 |
| 4,977,891 A | 12/1990 | Grim | 128/80 |
| 5,080,089 A * | 1/1992 | Mason | 601/15 |
| 5,113,877 A | 5/1992 | Johnson et al. | 128/882 |
| 5,125,400 A | 6/1992 | Johnson | 602/13 |
| 5,230,335 A | 7/1993 | Johnson et al. | 128/400 |
| 5,245,990 A * | 9/1993 | Bertinin | 601/152 |
| 5,411,541 A | 5/1995 | Bell et al. | 607/104 |
| 5,472,412 A | 12/1995 | Knoth | 602/26 |
| 5,496,262 A * | 3/1996 | Johnson | 602/13 |
| 5,591,200 A * | 1/1997 | Cone | 601/752 |
| 5,643,185 A | 7/1997 | Watson et al. | 602/26 |
| 5,782,856 A | 7/1998 | Flores-Valderrama | 606/201 |
| 5,792,084 A | 8/1998 | Wilson et al. | 602/13 |
| 5,813,144 A | 9/1998 | Prengler | 36/88 |
| 5,871,526 A | 2/1999 | Gibbs et al. | 607/104 |
| 5,928,273 A | 7/1999 | Schmidt | 607/104 |

FOREIGN PATENT DOCUMENTS

| | | |
|---|---|---|
| DE | 196 18 787 A1 | 11/1997 |
| FR | 2527435 | 12/1983 |

OTHER PUBLICATIONS

Nutech Advertisement, "Plexipulse All In 1 System", *Journal of Bone and Joint Surgery*, date unknown, but copyright 1996.

(List continued on next page.)

*Primary Examiner*—Michael A. Brown
(74) *Attorney, Agent, or Firm*—Ronald D. Faggetter; Mark R. Wisner

(57) ABSTRACT

A brace has a number of flexible compression bags filled with liquid disposed around the injured body part. The liquid is pressurized by a pump, which may be driven by muscle contracting or weight-bearing activities. The pump may provide a dynamic, oscillatory pressure, or a constant pressure, which pressure may be equal to the normal resting liquid pressure in the injured limb. The bags are segmented with valves allowing the liquid to flow in a controlled manner through the bags. The bags may be containing bags, or may be selectively placed to create pressures to resist specific injury effects and potential deformations when healing.

24 Claims, 12 Drawing Sheets

OTHER PUBLICATIONS

Extract from Jobst Advertising Brochure, "Compression: Orthopedics", Available at least by Jul. 1998.

Dale, P.A., J.T. Bronk and P.J. Kelly, "Fracture Healing with Elevated Venous Pressure", $35^{th}$ Annual Meeting, Orthopedic Research Society, Feb. 6–9, 1989, Las Vegas, pp 590–591.

"Aircast", Aircast Incorporated Brochure (Air–stirrup Braces, Pneumatic Armband, Patellar Brace, Infrapatellar Brace), undated; available at least by Jul. 1997.

"Aircast Walking Braces", Aircast Incorporated Brochure, undated; available at least by Jul. 1997.

"Pneumatic Achilles Wrap", Aircast Incorporated Brochure, undated; available at least by Jul. 1997.

"Aircast Pneumatic and Foam Walkers", Aircast Incorporated Brochure, no date, available at least by Jul. 1997.

"Aircast Air–stirrup Ankle Braces", Aircast Incorporated Brochure, no date, available at least by Jul. 1997.

Aircast Incorporated Brochure (Pneumatic Armband, Infrapatellar Band, Pneumatic and Foam Walkers, Air–Stirrup Ankle Braces), no date, available at least by Jul. 1997.

* cited by examiner

LIQUID BRACE

BACKGROUND OF THE INVENTION

The present invention relates to a liquid brace.

The human body is 60% water, and relies on atmospheric pressure and containing structures such as skin and muscle to maintain its fluids within its organs and to assist in the proper circulation of these fluids. Injury that disrupts these structures can allow the escape of fluid, causing further change. For example, the skin may be damaged by heat, cold or physical force. Fluid may as a result escape from internal body structures and cause swelling, which in turn may compromise the function of other structures such as veins, compounding the effect of the original injury. Similarly, since muscles aid the return of (blood and lymphatic) fluids to the lungs and chest by creating pressure during contraction, injury to muscles can therefore create additional circulatory problems. Muscles also support the bones they surround, and injury to muscles can result in a lack of support for bone structure during everyday activities. Thus, the purpose of containing devices for fluid in an injured or malfunctioning (i.e. Varicose Veins or Lymphoedema) limb is twofold: to minimize swelling; and to provide support to the limb.

This is reflected, for example, in the design of artificial limbs, where the sockets constrict the limb to contain the fluid muscle, fat and body fluids in the stump of the limb. In an above knee stump, the force of the body directed down the thigh bone (femur) is transferred to the artificial limb through resistance by the fluid pressure created by the socket.

However, sustained pressure or compression of liquid is harmful. For example, when tissue pressure is maintained above 25 mm of mercury then effective tissue perfusion is often terminated with severe consequences, as in "Compartment Syndrome".

There are known benefits to healing injuries in a normal activity environment. Healing at rest allows weak and poorly structured tissue to form, which must later be modified with secondary healing and/or therapy. This runs the risk of refracture, stiff joints or permanently weak ligaments. In contrast, healing in a normal activity environment creates stronger tissue, minimizes weakening of existing tissue, and often leads to earlier recovery. The usual barriers to healing in a normal activity environment are pain caused by swelling in the injured body area as well as the need for adequate structural support provided at the proper strength and at the right time and position to support weight-bearing activities.

Therapeutically effective pressure should therefore: (1) be cyclical, (2) mimic normal tissue pressure, and so (3) allow for normal activity while healing. Specifically, the normal resting liquid pressure in a body varies with the distance of a body part from the heart. Muscles acting around a limb create tremendous supporting pressures with normal activity and are vital to the support of bone, they also resist the escape of fluids from damaged tissue, and assist in the return of liquids to the heart. Furthermore, such pressures will be created at the appropriate time, such as when a load is placed upon a limb. Braces that can create or mimic such pressures thus allowing normal activity healing would aid in the speed and quality of the healing process for acute injuries.

A known difficulty is to design a brace that easily compensates for changes in the volume of an injured limb while avoiding potentially dangerous pressures. As a result, rigid and adjustable braces require frequent adjustment to be effective and not to cause damage. The "cast-brace" methods address this issue with frequent cast changes to compensate for swelling, reduction and musclewasting common to all injuries.

One known pressure device for Achilles tendon inflammation (the "pneumatic Achilles wrap" by Aircast Incorporated™) contains air bags on either side of the Achilles tendon connected to a bag placed beneath the foot. As the patient walks, the bag beneath the foot is compressed, inflating the bags around the Achilles tendon and increasing the pressure upon the tendon. When the foot lifts, the bags beneath the foot re-inflate and the pressure on the tendon is eased. This creates a cyclical high-low pressure. The level of resting, baseline or non-dynamic pressure may be decreased by allowing some of the air to escape from the brace through an external valve.

Braces are also known (the Plexipulse™ by NuTech,™ or various compression units by Jobst™) that extend along the length of an entire injured limb, such as a leg. These provide a plurality of air bags around the limb, each directly coupled to an electric pump which inflates them to create pressure. The pump may inflate the air bags serially to create a gradient of cyclic pressure along the length of the limb with a set resting pressure. However, the pump assembly is relatively complicated and expensive, and the patient's mobility is restricted when the brace is connected to the pump. This design is typically used for the treatment of chronic rather than acute injuries.

The pressures generated by these known devices may be insufficient to support injured tissues, especially during weight bearing or lifting.

SUMMARY OF THE INVENTION

The present invention provides, as part of a brace, at least one flexible compression bag, which may be partially distended with liquid, and placed against the injured body part. Through the use of valves and a pump, cyclic pressure may be created in the flexible compression bags, resulting in a cyclic pressure being applied to the injured body part.

In accordance with the present invention, there is provided a brace for supporting an injured body part of a wearer, comprising: at least one flexible compression bag adapted for holding a liquid; and a plurality of valves segmenting said at least one compression bag and arranged to provide liquid flow in a controlled manner through said at least one compression bag.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In the figures which illustrate example embodiments of the invention.

DETAILED DESCRIPTION OF THE PREFERRED EMBODIMENTS

The brace of this invention includes one or more flexible compression bags partially distended with liquid and placed around an injured body part, such as along the length of a limb. Through the use of valves and a pump, cyclic pressure may be created in the flexible compression bags, resulting in a cyclic pressure being applied to the injured body part. Different pumps and arrangements of compression bags are used in different embodiments to create various effects and advantages.

Figure 1:
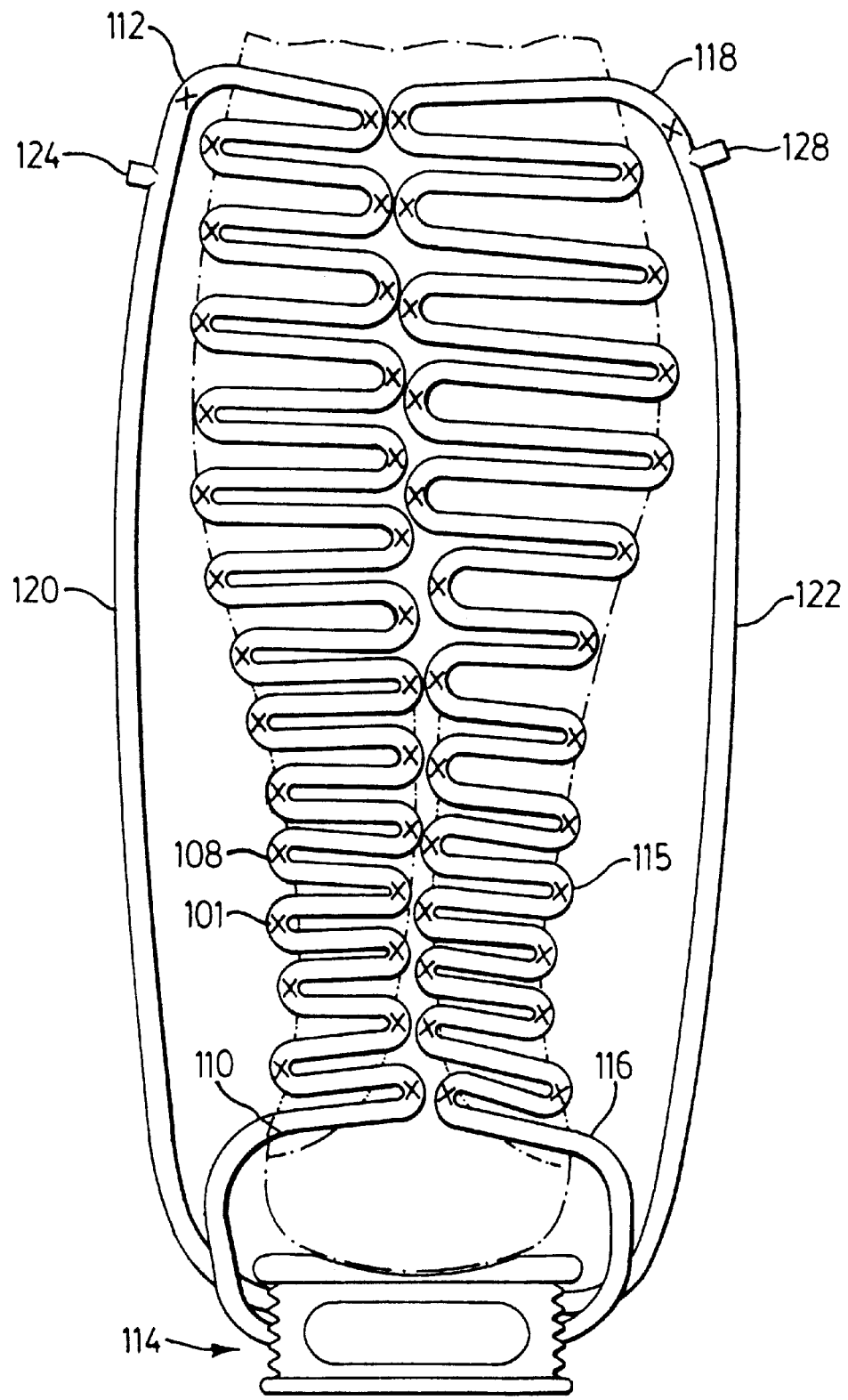
FIG. 1 is a back view of a brace for an injured calf muscle in accordance with this invention.
Figure 2:
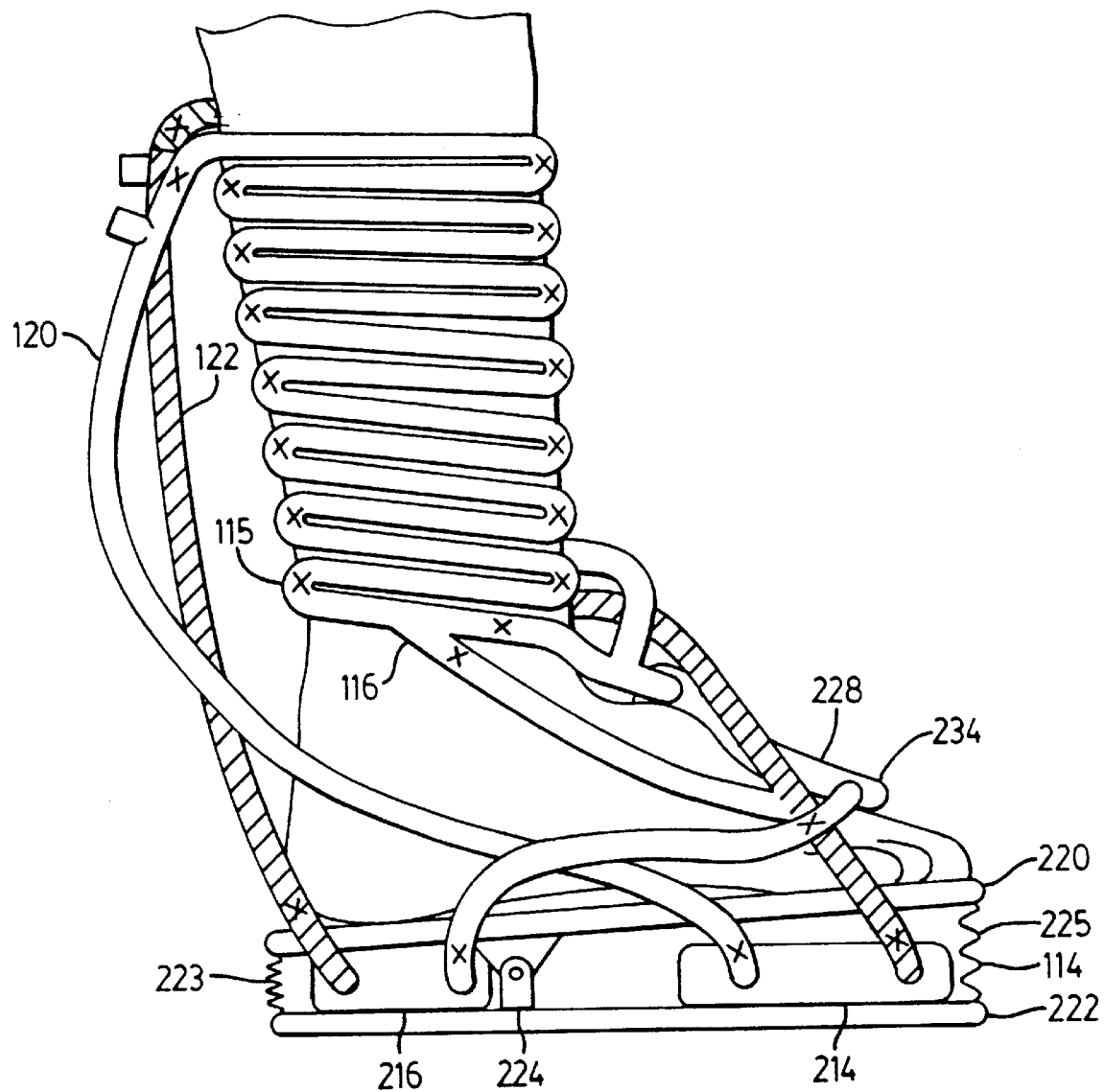
FIG. 2 is a side view of a portion of the brace of FIG. 1 detailing the pump which uses a wearer's walking motion to create an oscillatory pressure, in accordance with the invention.

An exemplary embodiment is illustrated in FIGS. 1 and 2 for a brace 106 covering the calf muscle from the ankle to just below the knee. Turning to FIGS. 1 and 2, a flexible compression bag 108 covers the left side of the injured calf muscle, and is segmented using a plurality of valves 101 to ensure that liquid flows in only the desired direction, that is, progressively from lower end inlet 110 of the bag to upper end outlet 112. The liquid emerges from the outlet 112 of the bag, and is returned to the lower end inlet 110 of the bag after passing through a return tube 120 and a pump 114, thus re-circulating the liquid. A second segmented flexible compression bag 115 covers the right side of the injured calf muscle, such that liquid will travel through the bag 115 from lower bag end inlet 116 to upper bag end outlet 118, and return through return tube 122 to pump 114, thus re-circulating the liquid. Return tubes 120 and 122 have filling ports 124 and 126 respectively, which open outside the brace.

As seen in FIG. 2, return tubes 120 and 122 connect into the bellows of pump 114. More specifically tube 120 connects into forward bellows bag 214 and tube 122 connects into rearward bellows bag 216. The outlet of forward bellows bag 214 connects to inlet 110 of compression bag 108 (not visible in FIG. 2) and inlet 116 of compression bag 115. The outlet of rearward bellows bag 216 connects to inlet 234 of (an optional) dorsum compression bag 228 which connects to the inlet 116 of compression bag 115 and inlet 110 of compression bag 108 (not visible in FIG. 2). When worn, forward bellows bag 214 is located under the sole of the foot and rearward bellows bag 216 under the heel of the foot. Bellows bags 214 and 216 are between bellows plates 220 and 222 which are pivotably connected at pivot 224 such that bellows bags 214 and 216 are alternately compressed and decompressed through a normal walking motion. Pivot 224 is located between bellow bags 214 and 216, and is located approximately at the center of gravity or center of weight-bearing when the brace is worn while standing. The ends of the bellows are covered with elastic accordion pleated ends 223, 225.

The liquid used is a suitable incompressible liquid, such as water. As air is a compressible fluid, the pressure that an air-based compression system can exert for a given complexity of compression equipment is limited. In comparison, liquids such as water are incompressible, and pressure can be exerted with much greater efficiency using a incompressible liquid-based compression system. However, liquid-based compression systems must be designed to ensure that too much pressure is not exerted at any particular time.

The compression bags 108 and 115 illustrated in FIGS. 1 and 2 are fabricated out of a flexible material such as poly-vinyl chloride. The bellows bags 214 and 216 illustrated in FIG. 2 may be made of the same material. The valves 101 can be one-way butterfly valves or one-way spring-loaded valves. Additionally, the valves could be solenoid valves controlled by one or more microchips or a computer.

Compression bags 108, 115 may be held against the injured body part by a nylon jacket, fastened around the injured leg through a zipper. If more support is required, plastic stays may be inserted to increase rigidity, or the housing of the brace may be made out of a rigid, inflexible material such as a hard plastic to provide structural support for the injured body part or protect the injured body part from unforseen external pressures. Tubes 122 and 120 should also be housed inside the nylon jacket with filling ports 124 and 126 extending outside the jacket, although alternatively tubes 120 and 122 may extend outside the nylon jacket.

Alternatively, flexible compression bags 108 and 115 are first held around the injured body part, and then a housing of the brace is placed around and attached to flexible compression bags 108 and 115 and tubes 120 and 122 to hold them in place and complete the machinery of the brace. Compression bags 108 and 115 may be distended to the desired amount by pumping in liquid through filling ports 124, 126.

In operation, a cyclic shockwave of pressure is created during walking that is proportional to the load put on the leg; the pressure peaks at the peak points of load bearing: when the heel strikes the ground; and when weight is placed on the front of the foot. This shockwave travels along the flexible compression bags from inlet 10 to outlet 112 of bag 108, and from inlet 116 to outlet 118 of bag 115, respectively. Both the pressure exerted by gravity and the cyclic shockwave pressure may be regulated by adjusting the amount of liquid in the brace through filling ports 124 and 126. By using valves 101 (one-way, or alternatively controlled solenoid valves), the baseline or resting pressure exerted by gravity at the lowermost part of the brace may be reduced, preventing potentially dangerous pressures from forming. In this manner, the brace produces pressure more akin to normal body liquid pressure, potentially leading to more efficient healing of the enclosed limb. The brace exerts a cyclic pressure on the injured muscle without the use of external pumps that inhibit the mobility of the patient. In addition, the use of a manual pump implies that the brace 106 will be easier to make and maintain than a brace with a non-manual pump.

If solenoid valves are used, the microcontrollers for these valves may use as inputs signals from proximity sensors or microswitches 250 located in the bellows. The microcontrollers may time the opening of the valves to control the pressure throughout the system.

Figure 3:
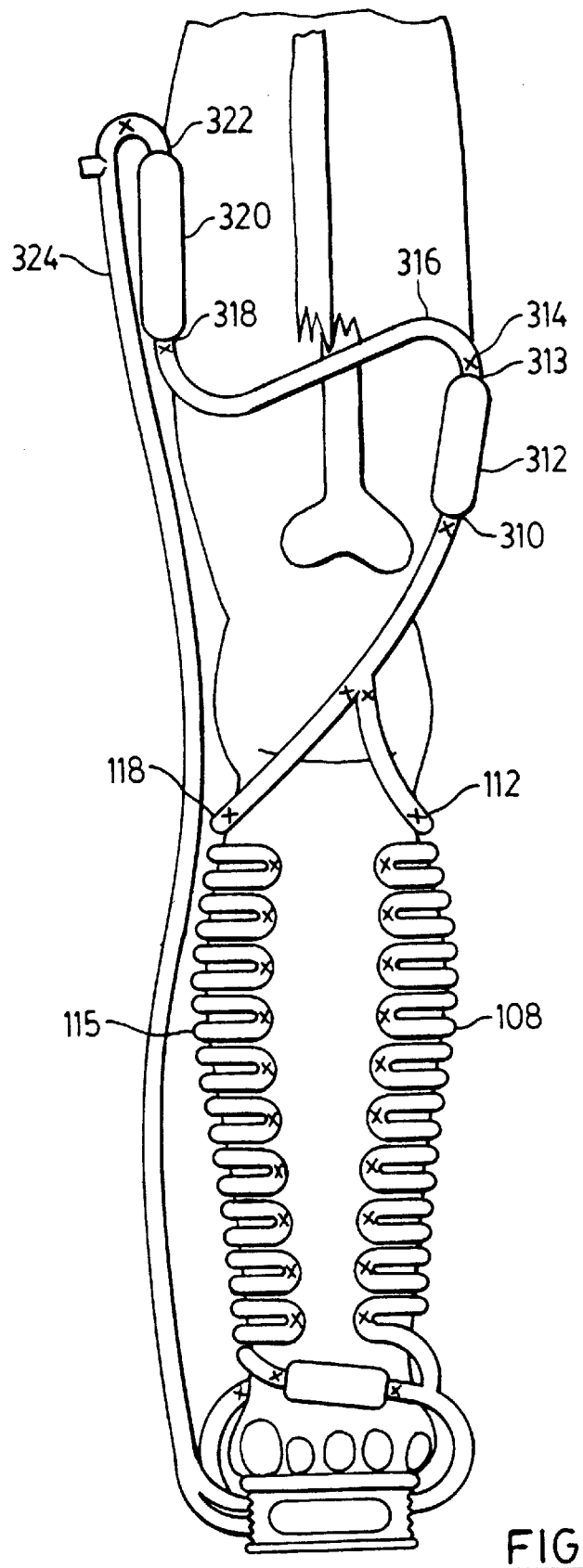
FIG. 3 is a front view of the brace of FIG. 1 with two additional thigh compression bags added to correct a femur bone displacement, in accordance with the invention.

At least one bag may be added to the thigh area to take the liquid after the main calf area bags before returning the liquid via the return tubes to the foot. These thigh compression bags may be arranged to provide benefits for specific types of injuries, such as fractures where deforming forces can be neutralized, or localized burns. Such an arrangement is illustrated in FIG. 3 for a broken femur bone. In FIG. 3, the brace, including compression bags and pump, is similar to the embodiment of FIGS. 1 and 2, and like parts have been given like numbers. Turning to FIG. 3, upper end outlets 112, 118 of compression bags 108 and 115 are connected to inlet 310 of outer thigh compression bag 312. Outlet 313 of outer thigh compression bag 312 is connected to inlet 318 of inner thigh compression bag 320 by tube 316. Outlet 322 of inner thigh compression bag 320 is connected via return tube 324 to forward and rearward bellows bags 214 and 216 (not shown in FIG. 3). The system contains a plurality of one-way valves 314.

In operation, the lower assembly of the brace in FIG. 3 operates in a similar manner to the brace in FIGS. 1 and 2. The plurality of one-way valves 314 ensure that the liquid flows from outlets 112 and 118 through outer thigh compression bag 312, then through tube 316 and inner compression bag 322 before returning through return tube 324 to pump 114. When the brace is pressurized, outer thigh compression bag 312 presses in upon the broken femur bone below the fracture, and inner thigh compression bag 320 presses the broken femur bone outwards above the fracture. This helps to align the femur bone and support it in a proper position during the peak times of weight bearing: when the heel strikes the ground; and when weight is placed on the front of the foot. The plurality of one-way valves 314 as well as the amount of liquid in the brace may be designed to control the quantum of pressure being exerted by thigh bags 312 and 320.

Figure 4:
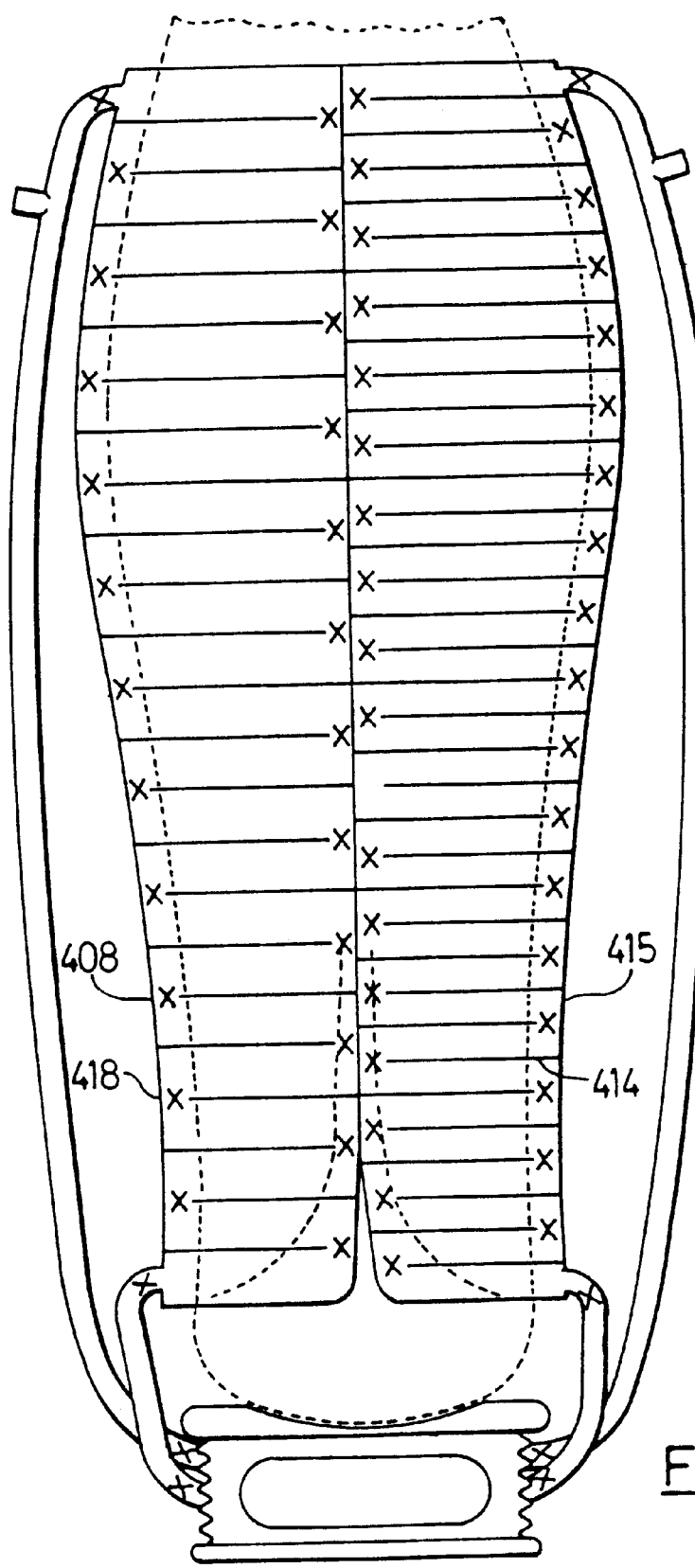
FIG. 4 is a back view of a brace for an injured calf muscle with an alternative compression bag arrangement, in accordance with the invention.

In FIG. 1, a given compression bag (108 or 115) is layered over a particular injured area so as to completely cover that injured area. An alternative arrangement for the compression bags in the brace of FIG. 1 is illustrated in FIG. 4. Turning to FIG. 4, the compression bags 408 and 415 are structured with channels created in the bag itself through heat sealing or some other appropriate method to create a plurality of internal walls 414. A plurality of valves 418 ensure that liquid flows through the bags in a controlled manner.

Figure 5:
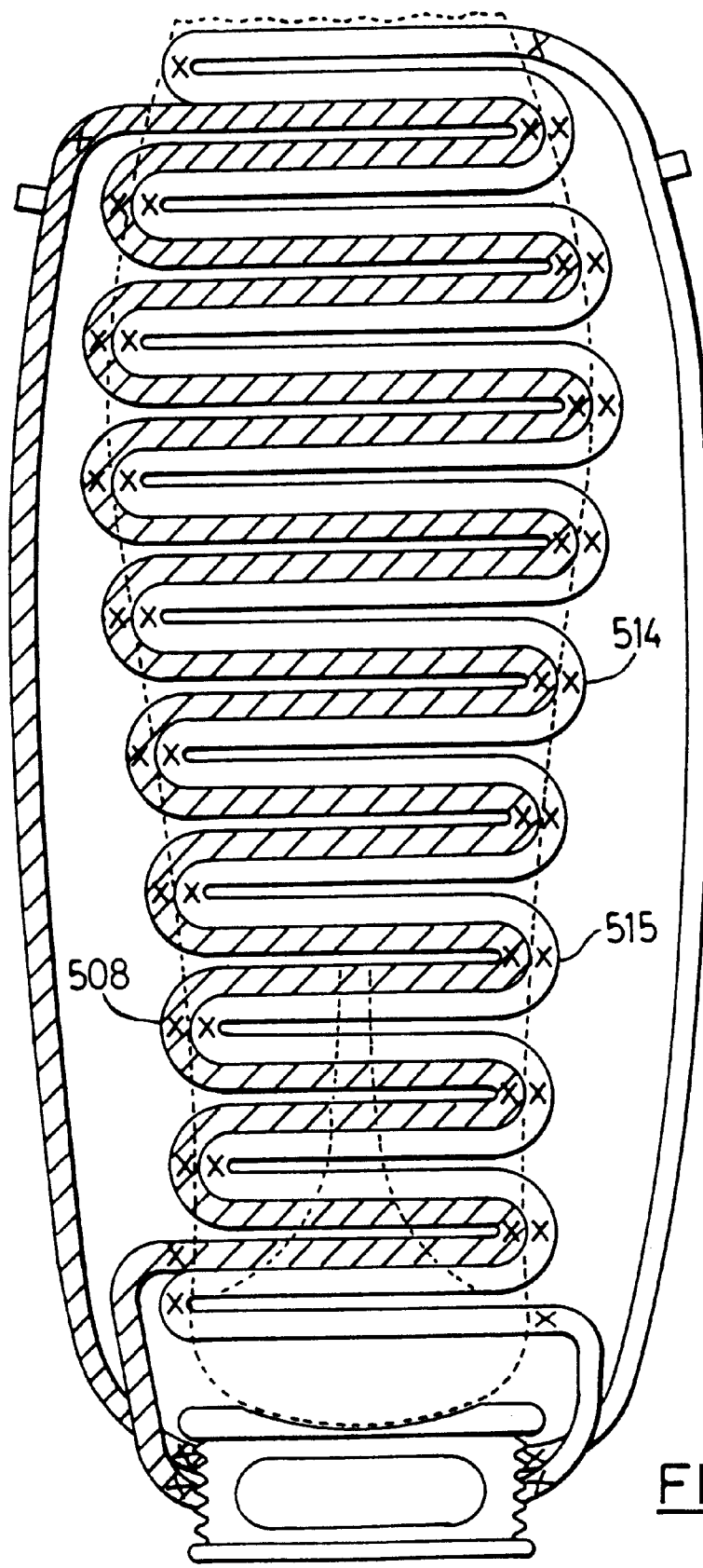
FIG. 5 is a back view of a brace for an injured calf muscle with an alternative compression bag arrangement, in accordance with the invention.

Another alternative arrangement for the compression bags in the brace of FIG. 1 is illustrated in FIG. 5. Turning to FIG. 5, compression bags 508 and 515 are inter-wound over the injured area, so as to completely cover the injured area. A plurality of valves 514 ensure that liquid flows through the bags in a controlled manner.

Figure 6:
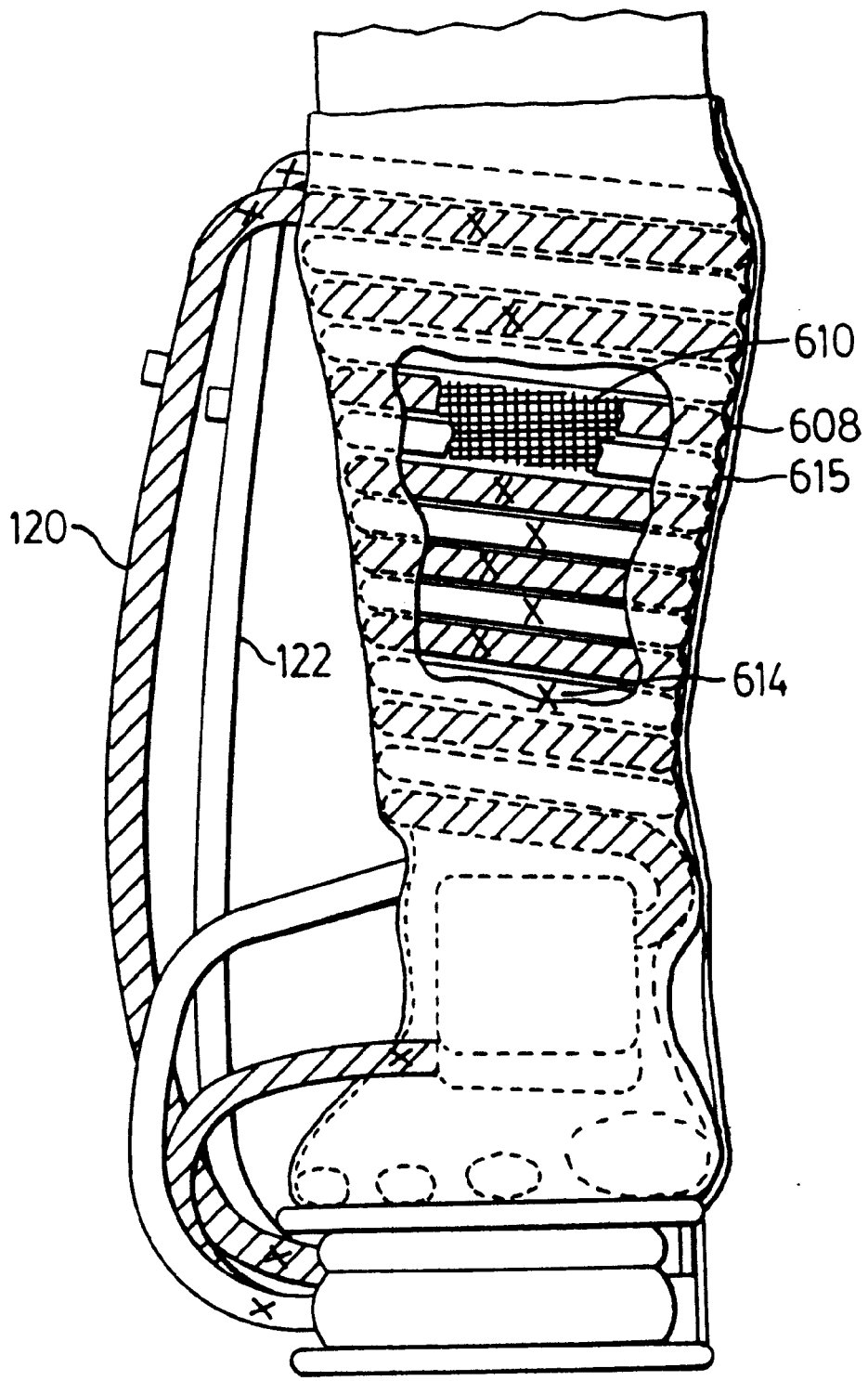
FIG. 6 is a front view of a brace for an injured calf muscle with an alternative compression bag arrangement, in accordance with the invention.

Another alternative arrangement for the compression bags in the brace of FIG. 1 is illustrated in FIG. 6. Turning to FIG. 6, compression bags 608 and 615 wrap around and substantially cover the injured calf muscle, and are segmented by a plurality of valves 614 to ensure that liquid flows through the bags in a controlled manner.

If the brace is of the configuration illustrated in FIG. 6, the compression bags may be sewn together in an annular configuration then put in place or removed by the wearer after emptying flexible compression bags 608, 615 to permit the brace to be slipped on or off the injured body part. The compression bags may be emptied by opening filling ports 124 and 126 and operating bellows 211 to discharge the liquid through filling ports 124, 126. Otherwise, the operation of the embodiments of FIGS. 4 to 6 is the same as that described in conjunction with FIGS. 1 to 3. Although the tubes 120, 122 are diagrammed in FIG. 6 as external to the covering for clarity, in most embodiments the tubes will be placed inside the external covering.

Preferably, there is a layer 610 of material, such as cloth, between the surface of compression bags 608 and 615 and that allows the skin to breathe naturally whilst not blunting the compression pressure exerted by compression bags 608 and 615.

Figure 7:
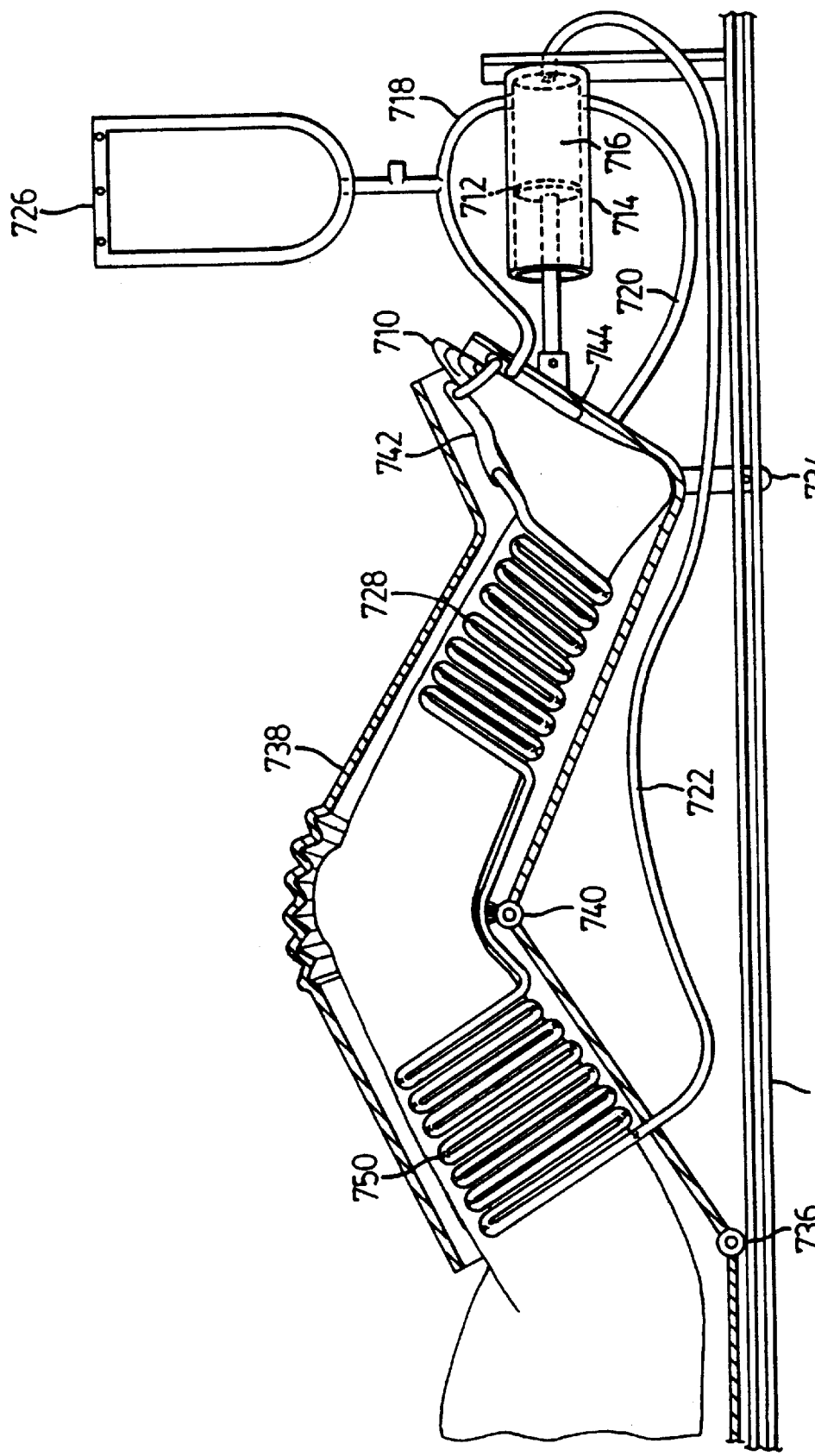
FIG. 7 is a side view of a brace for an injured leg that uses a deliberate motion by the wearer to create an oscillatory pressure, in accordance with the invention.

FIG. 7 illustrates a brace 706 applied to an entire leg that utilizes a deliberate movement of the patient to generate the liquid pressure. Turning to FIG. 7, plunger 712 is connected to liquid-filled pump cylinder 714. Pump cylinder 714 is connected by tube 718 to a first segmented flexible compression bag 728. This bag extends along the bottom of the injured leg, leaves the knee area exposed, extends along the top of the injured leg above the knee, and connects to return tube 722. The pump cylinder is connected by tube 720 to a second flexible compression bag 730 (not shown), which similarly extends along the other side of the leg. The illustrated configuration of the bags is that shown in FIG. 1, but the configurations illustrated in any of FIGS. 4, 5 and 6 could equally be employed. The tubes and bags are segmented by a plurality of one-way valves 750. The housing 738 of brace 706 is connected to a base 732 by pivot 736 and key 734. The housing 738 also has a medial pivot 740 positioned under the knee of the wearer. Key 734 fits into a keyway in base 732 so that key 734 may slide back and forth along base 732 in a direction permitted by cylinder 714 and pivots 736 and 740. In operation, reciprocal movement of the wearer's foot 710 reciprocates plunger 712 in cylinder 714, cyclically creating a pressure in liquid 716 which pressure, in turn, is transmitted to flexible compression bags 728 and 730. Valves 750 may be designed to ensure that liquid travels only in the direction described above. Flexible bags 742 and 744 may be added on top of and under the foot, if desired.

Optionally, a somewhat elastic reservoir 726 may be provided to moderate the applied pressure.

This embodiment of the invention allows the wearer to actively create a cyclic pressure along the injured area, and is useful where aggressive pressure stimulation is required to promote active fluid flow and a reduction of swelling in the injured area.

Persons skilled in the art will appreciate that there are numerous possible pump mechanisms which will have a similar effect to pump cylinder 714. Also, the apparatus in FIG. 7 could be incorporated as part of a continuous passive motion machine, where a motor would move key 734 back and forth in an oscillatory manner in the keyway along base 732, flexing the leg and operating pump cylinder 714 while the patient is resting or sleeping.

Figure 8:
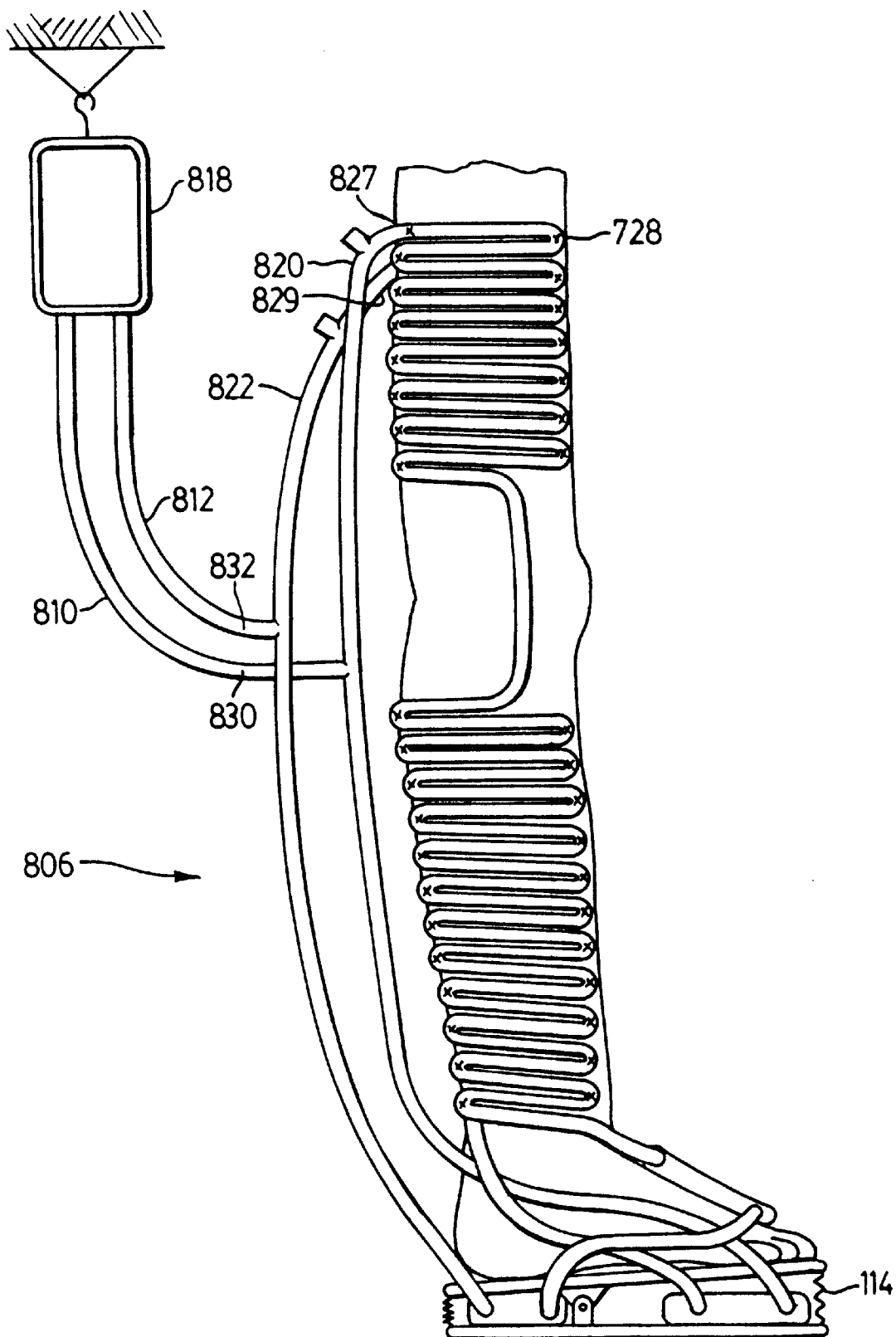
FIG. 8 is a side view of a brace for an injured leg that uses a liquid bag to produce a baseline pressure, in accordance with the invention.

FIG. 8 illustrates a brace 806, which exerts a static resting pressure on the injured body part. The brace of FIG. 8 contains compression bags similar to that of FIG. 7 with a pump similar to that of FIGS. 1 and 2, and like parts have been given like reference numbers. In brace 806, return tubes 820 and 822 are connected between ends 827, 829 of bags 728, 730 respectively, and pump 114. Branch tubes 810 and 812 are connected at one end to ports 830, 832 attached to return tubes 820 and 822, and at their other end to a static pressure bag 818 which might be a soft-walled partially filled intravenous bag.

In operation, a constant baseline pressure is maintained in flexible compression bags 728 and 730, proportional to the height of static pressure bag 818. In this manner, the brace 806 can automatically adjust to changes in volume of an injured limb while avoiding potentially dangerous pressures. By elevating or lowering static pressure bag 818 to a level the same height as the patient's heart, a pressure equal to the resting tissue pressure may be maintained. The pressure may also be lowered or raised, by lowering or raising static pressure bag 818, dependent on the wearer or doctor wishing to change the degree of support or the tissue perfusion.

It will be appreciated by those skilled in the art that the same overall effect could be created by a static pressure pump attached to the brace without the presence of static pressure bag 818.

Figure 9:
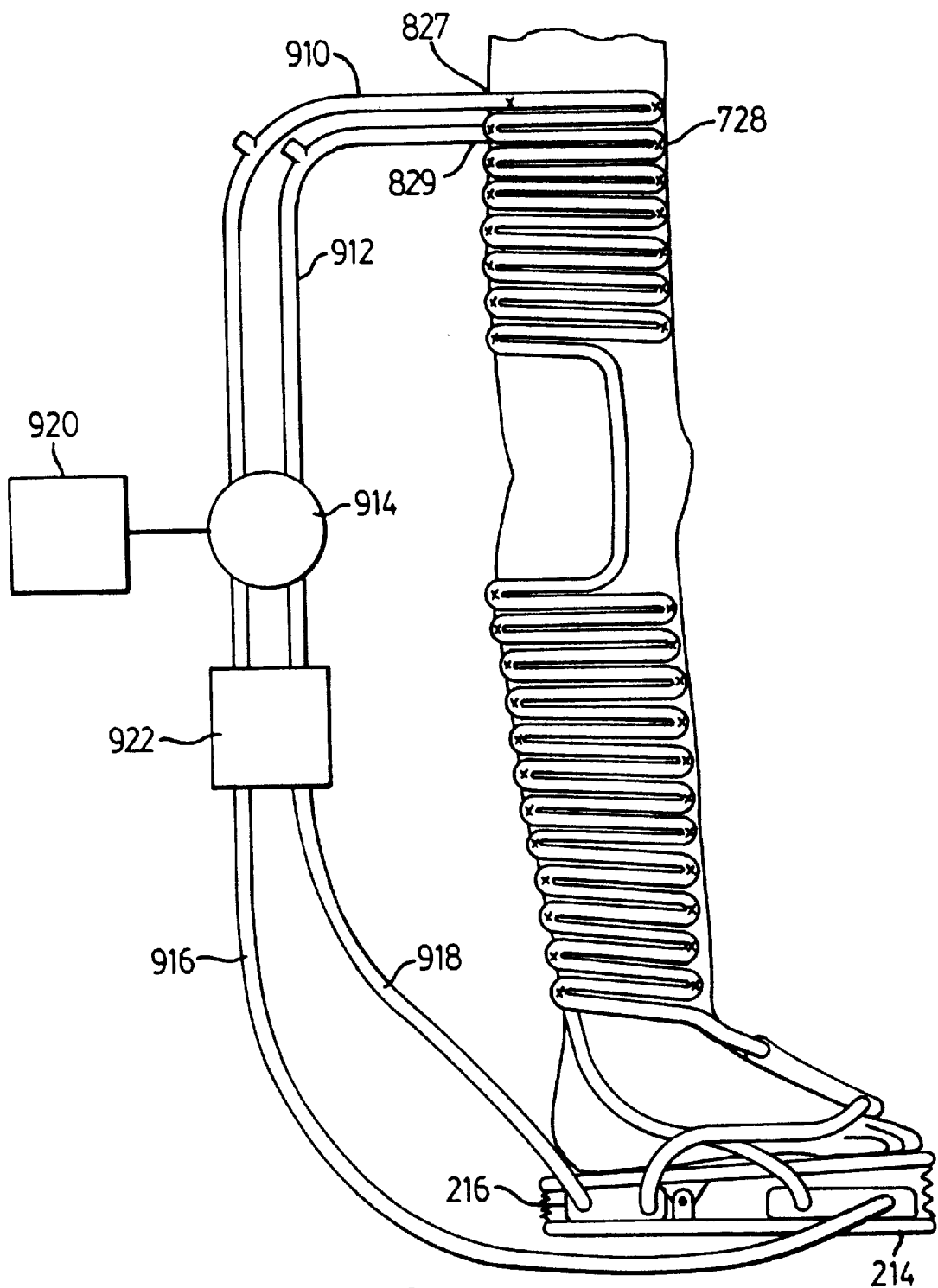
FIG. 9 is a side view of a brace for an injured leg that uses an attached electric pump to produce a constant or cyclical pressure, with the pumped liquid being of a controlled temperature, in accordance with the invention.

If a dynamic, cyclical pressure is desired, an electric pump may be attached to the brace to create the desired oscillatory pressure as shown in FIG. 9. The brace of FIG. 9 is similar to that of FIG. 8, and like parts have been given like reference numbers. Turning to FIG. 9, return tubes 910 and 912 are connected between ends 827, 829 of bags 728, 730 respectively, and electric pump 914. Electric pump 914 is connected by tubes 916 and 918 to forward bellows bag 214 and rearwards bellows bag 216 respectively. This electric pump 914 may be controlled by a controller 920 to generate a pulse of pressure at a rate and quantum typical of an average heartbeat. The brace could also, optionally, include a heating/cooling coil 922 to control the temperature of the liquid being pumped into tubes 916 and 918. It should be noted that liquids are much more efficient heat transfer agents than air, and the invention would therefore apply heating or cooling to a braced body part more efficiently than an air-based brace.

It will be appreciated by those skilled in the art that such a pump could be incorporated into a continuous passive motion machine, which thus could manipulate a damaged limb whilst simultaneously creating a cyclic pressure on the injured limb of a desired temperature.

Figure 10:
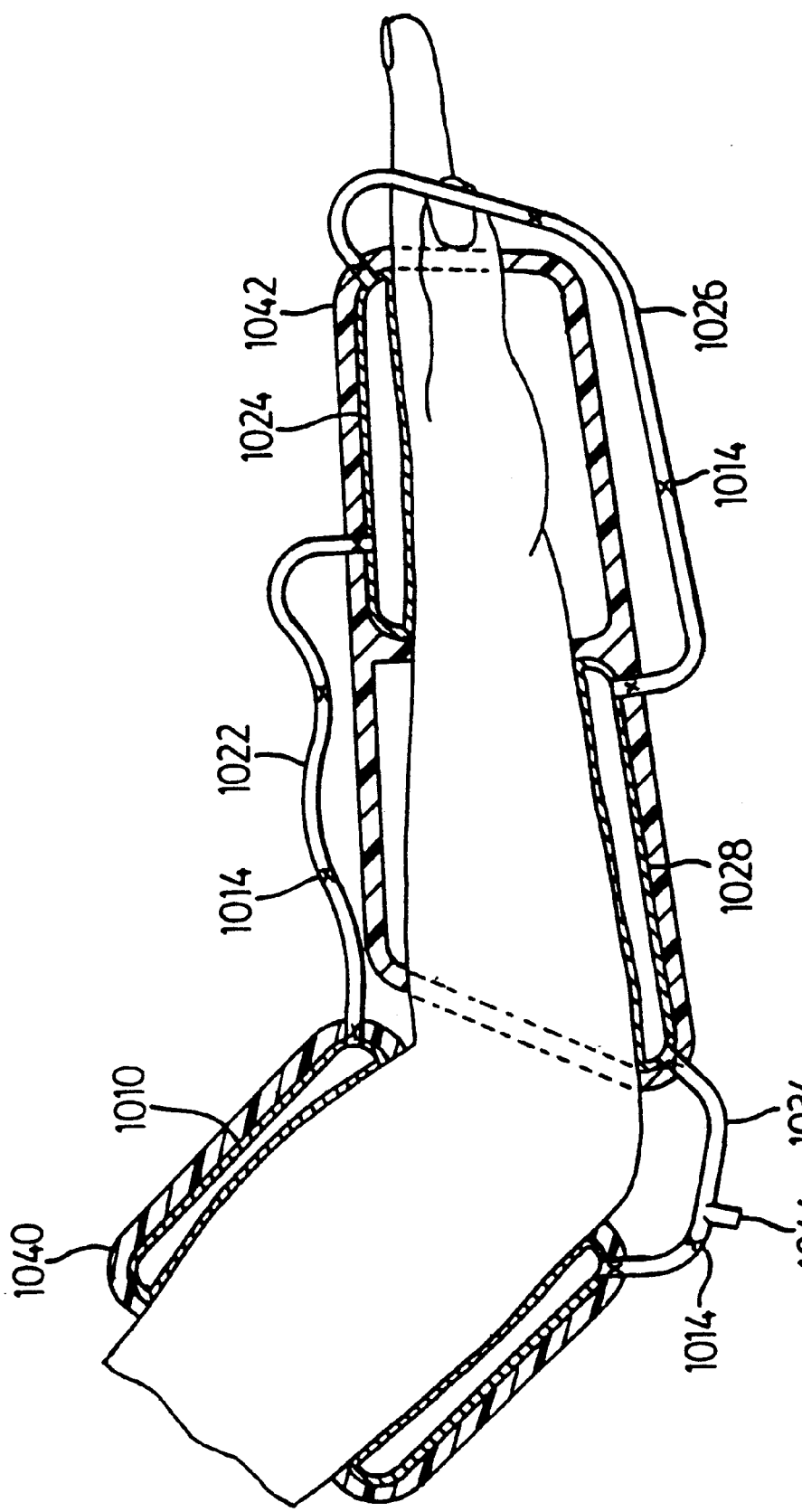
FIG. 10 is a side view of a brace for an injured forearm that uses the natural bulking of the muscles of a healthy upper arm to produce pressure to assist the injured forearm in weight-bearing activities, in accordance with the invention.

FIG. 10 illustrates a brace where muscle contraction in a healthy body part, the upper arm, is used as a pump to create pressure in a desired manner in a brace covering an injured body part, the lower arm. Turning to FIG. 10, an annular flexible bag 1010 encircles the upper part of an arm. Tube 1022 connects bag 1010 to flexible bag 1024, and contains a plurality of one way valves 1014 to ensure that liquid flows only from bag 1010 to bag 1024. Tube 1026 connects flexible bag 1024 to flexible bag 1028, and contains a plurality of one way valves 1014 to ensure that liquid flows only from bag 1024 to bag 1028. Tube 1034 connects flexible bag 1028 to flexible bag 1010, and contains a plurality of one way valves 1014 to ensure that liquid flows only from bag 1028 to bag 1010. Bag 1010 is contained by an outer housing 1040. Bags 1024 and 1028 are contained within an outer housing 1042, which may be rigid to provide support or protection for the injured body part. Tube 1034 has filling port 1044, which opens outside the brace.

In operation, muscle contraction of the upper arm creates pressure in the liquid in bag 1010. This liquid travels via tube 1022 to bag 1024, creating an increase in pressure in bag 1024. Liquid from bag 1024 travels via tube 1026 to bag 1028, creating an increase in pressure in bag 1028. Finally, liquid travels from bag 1028 toward bag 1010 via tube 1034, thus re-circulating the liquid.

If the person wearing the brace has a Colles type fracture, bag 1024 may be placed over the fracture near the wrist, and bag 1028 may be placed on the forearm near the elbow. When the wearer uses their arm to pick up an object, the contraction in the upper arm causes bags 1024 and 1028 to put pressure on the forearm and resist displacement of the fracture simultaneously with a load being placed on the injured limb. By selecting a proper size of bag 1010, the pressure exerted by bags 1024 and 1028 may be adjusted to be appropriate for the loads which will be placed upon the injured body part. Valves 1014 may be designed to moderate and control the dynamic application and release of this pressure.

Figure 11:
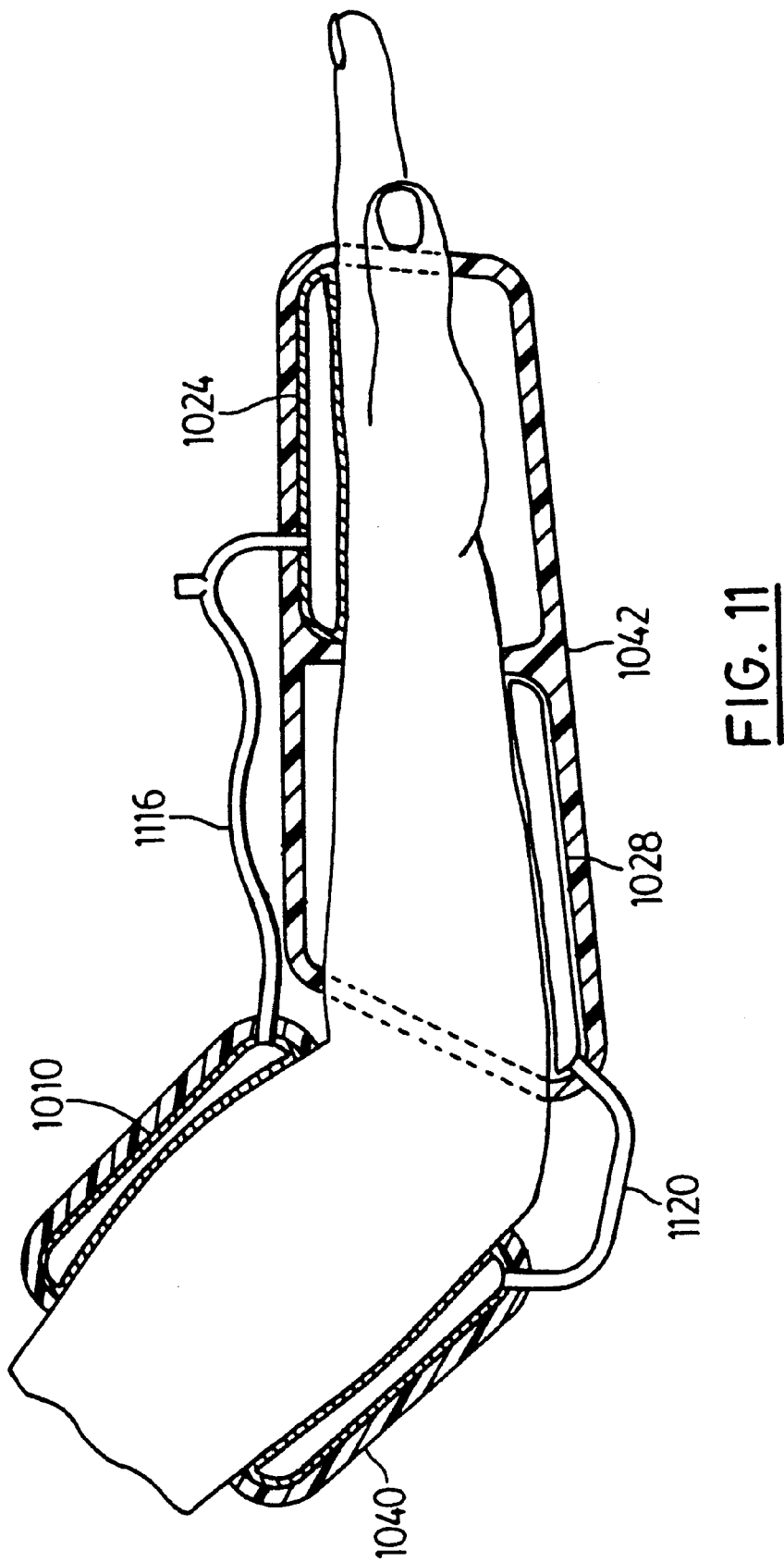
FIG. 11 is a side view of another brace for an injured forearm that uses the natural bulking of the muscles of a healthy upper arm to produce pressure to assist the injured forearm in weight-bearing activities, in accordance with the invention.

A similar embodiment is illustrated in FIG. 11, except that it omits the one-way valves and tube 1026. Turning to FIG. 11, an annular flexible bag 1010 encircles the upper part of the arm. Tube 1116 connects flexible bag 1010 to flexible compression bag 1024, while tube 1120 connects flexible bag 1010 to flexible compression bag 1028. Bag 1010 is contained in outer housing 1040. Bags 1024 and 1028 are contained in outer housing 1042, which may be rigid to provide support or protection for the injured body part.

In operation, if the person wearing the brace has a Colles type fracture (created by falling on an outstretched hand), bag 1024 may be placed over the fracture near the wrist, and bag 1028 may be placed on the forearm near the elbow. When the wearer uses their arm to pick up an object, the contraction in the upper arm causes bags 1024 and 1028 to put pressure on the forearm, creating a "three point pressure" and resisting displacement of the Colles fracture simultaneously with a load being placed on the injured limb. By selecting a proper size of bag 1010, the pressure exerted by bags 1024 and 1028 may be adjusted to be appropriate for the expected loads being placed upon the injured body part.

It will be appreciated by those skilled in the art that the compression bags could be placed in a manner appropriate to different fracture types, especially in cases where deforming forces can be neutralized or tissue damage is localized.

Optionally, an extra pump, such as a hand pump, may be used to increase the pressure exerted by the compression bags upon the injured area.

Figure 12:
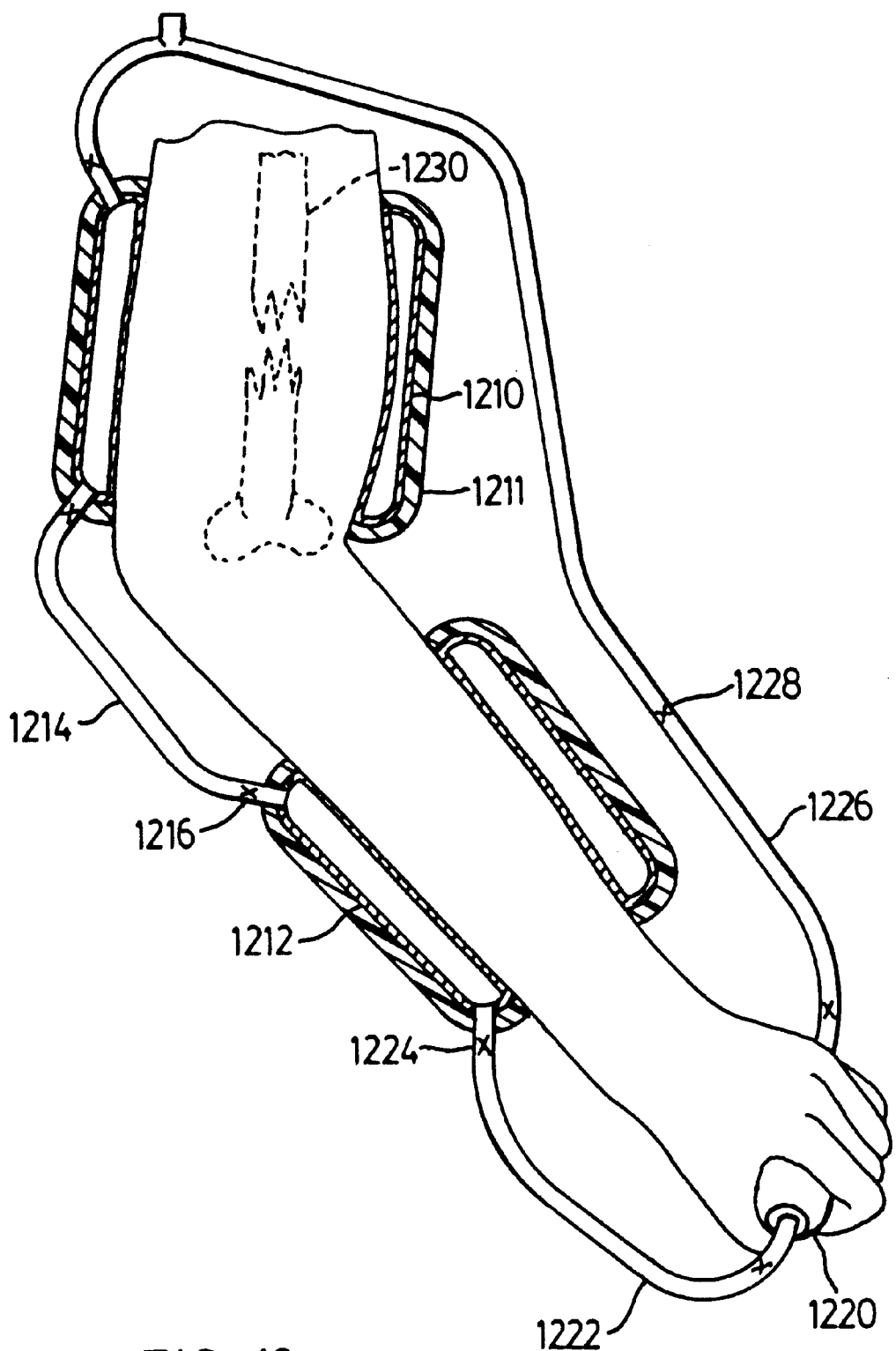
FIG. 12 is a side view of a brace for a broken humerus that uses the natural bulking of the muscles of a healthy forearm in series with a hand pump to produce pressure to assist the upper arm in weight-bearing activities and correct outward bowing, in accordance with the invention.

FIG. 12 illustrates this option. Turning to FIG. 12, a compression bag 1210 is placed against the outer arm of the patient, and is held within an outer housing 1211, which may be rigid to provide support or protection for the injured body part. The injured body part illustrated in this figure is a fractured humerus 1230. A second compression bag 1212 forms an annulus and surrounds the forearm. Compression bags 1210 and 1212 are connected by tube 1214, which contains a plurality of one-way valves 1216. Forearm compression bag 1212 is connected to hand pump 1220 by tube 1222 containing a plurality of one-way valves 1224. Hand pump 1220 is connected to compression bag 1210 by tube 1226, which contains a plurality of one-way valves 1228.

In operation, when a weight is placed upon the arm, the muscles in the forearm will bunch up, creating an increase in pressure which is transmitted through tube 1214 to compression bag 1210 through the operation of one-way valves 1216 and 1218. In addition, the pressure generated by the bunching of the forearm muscles may be supplemented by pumping hand pump 1220, increasing the pressure in forearm compression bag 1212 and in turn compression bag 1210. Finally, the liquid exits compression bag 1210 via tube 1226 and returns to hand pump 1220. In tube 1226, the flow of liquid is controlled by a plurality of one-way valves 1228.

In this manner, pressure and support is provided to the injury to the upper arm simultaneously with weight-bearing stress. Hand pump 1220 and forearm compression bag 1212 can be sized and valves 1216, 1224 and 1226 can be designed to deliver the correct amount of pressure through compression bag 1210. Furthermore, by placing compression bag 1210 on the outside of the upper arm, compression bag 1210 will act to resist outward bowing (varus angulation) of the fractured humerus 1230.

In FIG. 12, hand pump 1220 and forearm compression bag 1212 are connected in series to produce pressure in compression bag 1210. Alternatively, hand pump 1220 could be attached to compression bag 1210 in parallel with forearm compression bag 1212 to produce pressure in compression bag 1210.

In the embodiments shown in FIGS. 10 and 11, the healthy body part is higher than the injured body part. In FIG. 10, the volume of liquid in bag 1010 encompassing the healthy body part will serve to maintain a resting pressure in bags 1024 and 1028 to support the injured body part. Similarly, in FIG. 11, the volume of liquid in bag 1010 encompassing the healthy body part will serve to maintain a resting pressure in bags 1024 and 1126 to support the injured body part. If it is likely that the healthy body part covered by bag 1010 or, in FIG. 12, bag 1212, will be lower than the injured body part for significant amounts of time, an elevated static pressure reservoir similar to that illustrated in FIG. 8 could be used to provide an appropriate resting pressure.

From the foregoing, it will be apparent that the choice of position for the bags of a brace will be dependent upon the injury suffered by the body part so that the brace can achieve specific controlling forces to neutralize the effects of the injury.

The term "bag" as used throughout denotes any flexible walled container.

Other modifications within the spirit of the invention will be apparent to those skilled in the art.

What is claimed is:

1. A brace for supporting an injured body part of wearer, comprising:
   at least one flexible compression bag containing a liquid;
   a plurality of valves, each valve having a first open position and a second closed position, said valves segmenting said at least one compression bag into serially arranged bag sections and arranged to provide liquid flow in a controlled manner through said at least one compression bag.

2. The brace of claim 1, further comprising a pump for pumping liquid through said at least one compression bag.

3. The brace of claim 2, wherein said valves are one-way valves or computer controlled solenoid valves.

4. The brace of claim 2 wherein said pump comprises an electric pump having a control for controlling the temperature of the liquid exiting from the pump.

5. The brace of claim 2 wherein said pump comprises at least one flexible compression bag forming at least a portion of an annulus for encircling a healthy body part which expands on muscle contraction.

6. The brace of claim 2 further comprising at least one return tube such that an outlet of each of said at least one compression bag is connected to an inlet of said pump whereby said pump re-circulates liquid in said at least one compression bag.

7. The brace of claim 2 wherein said pump comprises a manually operated cylinder.

8. The brace of claim 2 wherein said pump comprises an electric pump having a control for generating a pulse of liquid at a selected rate and quantum mimicking a heart rate of a wearer.

9. The brace of claim 2 wherein said pump comprises a continuous passive motion machine.

10. The brace of claim 2 including a port for, when open, allowing liquid to be admitted or discharged from said at least one compression bag.

11. The brace of claim 2 wherein said at least one compression bag forms an annulus for reception of the injured body part.

12. The brace of claim 2 further comprising a layer of material surrounding said at least one compression bag, said material allowing the skin to breathe naturally when said at least one compression bag is placed against the skin.

13. The brace of claim 2 wherein said at least one compression bag comprises at least two compression bags.

14. The brace of claim 16 wherein said brace comprises a housing for releasably holding said at least two compression bags about an injured body part of a wearer.

15. The brace of claim 1 wherein said liquid is water.

16. The brace of claim 1 wherein said at least one flexible compression bag comprises segments disposed one above another such that, but for said valves, gravity acting on said liquid would elevate pressure in lower ones of said segments higher than in upper ones of said segments.

17. The brace of claim 1 wherein said at least one flexible compression bag is partially distended by said liquid so as to apply a resting pressure.

18. A brace for supporting an injured body part of a wearer, comprising:
   at least one flexible compression bag adapted for holding a liquid;
   a plurality of valves segmenting said at least one compression bag and arranged to provide liquid flow in a controlled manner through said at least one compression bag;
   a pump for pumping liquid through said at least one compression bag
   a liquid reservoir in fluid communication with said at least one flexible compression bag for providing a static pressure in said at least one compression bag.

19. A brace for supporting an injured body part of a wearer, comprising:
   at least one flexible compression bag adapted for holding a liquid;
   a plurality of valves segmenting said at least one compression bag and arranged to provide liquid flow in a controlled manner through said at least one compression bag;
   a pump for pumping liquid through said at least one compression bag
   wherein said pump comprises a pivoted pump plate with the pivot located approximately at the center of weight-bearing when a wearer of the brace is standing and a pair of flexible pump bags, one on each side of said pivot, each pump bag connected between an inlet and outlet of at least one of said at least one compression bag, said pump plate arranged for attachment to a foot of the wearer such that, in use, one pump bag is disposed under a sole of said wearer and another pump bag is disposed under a heel of said wearer.

20. The brace of claim 19 wherein said valves are solenoid valves and further comprising solenoid valve actuators associated with said bellows.

21. The brace of claim 20 wherein said solenoid valve actuators comprise proximity sensors or microswitches.

22. A brace for supporting an injured body part of a wearer, comprising:

- at least one flexible compression bag adapted for holding a liquid;
- a pump;
- conduit extending between said at least one flexible compression bag and said pump;
- said pump comprising an annular member adapted for encircling a healthy body part which expands on muscle contraction, said annular member comprising a flexible pump bag such that upon muscle contraction, liquid is pumped from said flexible pump bag to said at least one flexible compression bag, said brace further comprising a plurality of valves, each valve having a first open position and a second closed position, said valves segmenting said at least one compression bag and arranged to provide liquid flow in a controlled manner through said at least one compression bag.

23. The brace of claim 22 wherein said at least one compression bag forms an annulus for reception of the injured body part.

24. The brace of claim 22 further comprising at lest one return conduit such that an outlet of each of said at least one flexible compression bag is connected to an inlet of said pump whereby said pump re-circulates liquid in said at least one flexible compression bag.

* * * * *